United States Patent
Hoepffner et al.

(12) 
(10) Patent No.: US 6,530,943 B1
(45) Date of Patent: Mar. 11, 2003

(54) SURGICAL NEEDLE FOR IMPLANTING A TAPE

(75) Inventors: Hans-Jochen Hoepffner, Belle Mead, NJ (US); Jorn Lehe, Hamburg (DE)

(73) Assignee: Ethicon, GmbH (DE)

( * ) Notice: Subject to any disclaimer, the term of this patent is extended or adjusted under 35 U.S.C. 154(b) by 59 days.

(21) Appl. No.: 09/716,685

(22) Filed: Nov. 20, 2000

(30) Foreign Application Priority Data

Dec. 15, 1999 (DE) .......................... 199 61 218

(51) Int. Cl.⁷ .............................. A61B 17/06
(52) U.S. Cl. .................................. 606/222
(58) Field of Search ................. 606/222, 224, 606/223

(56) References Cited

U.S. PATENT DOCUMENTS

| | | | |
|---|---|---|---|
| 2,841,150 A | | 7/1958 | Riall |
| 5,478,327 A | * | 12/1995 | McGregor et al. .......... 604/272 |
| 5,549,629 A | * | 8/1996 | Thomas et al. ............. 606/223 |
| 5,649,961 A | * | 7/1997 | McGregor et al. .......... 606/222 |
| 5,683,416 A | * | 11/1997 | McGregor et al. .......... 606/223 |

FOREIGN PATENT DOCUMENTS

| | | |
|---|---|---|
| DE | 3712163 | 10/1988 |
| DE | 69014786 | 6/1995 |
| EP | 0286438 | 6/1993 |
| EP | 0404018 | 7/1995 |
| SU | 1178420 | 2/1984 |

* cited by examiner

Primary Examiner—John J. Calvert
Assistant Examiner—Katherine Moran

(57) ABSTRACT

A surgical needle (1) for implanting a tape (2) has a needle tip (12) at the distal end (10) of the needle (1) and a shaft (14). An insertion wing (20) with a distal (24) and a proximal (26) end extends from the shaft (14). The insertion wing (20) widens from its distal end (24) in proximal direction and has in the area of its proximal end (26) an attachment device (32) for the tape (2) to be implanted.

18 Claims, 2 Drawing Sheets

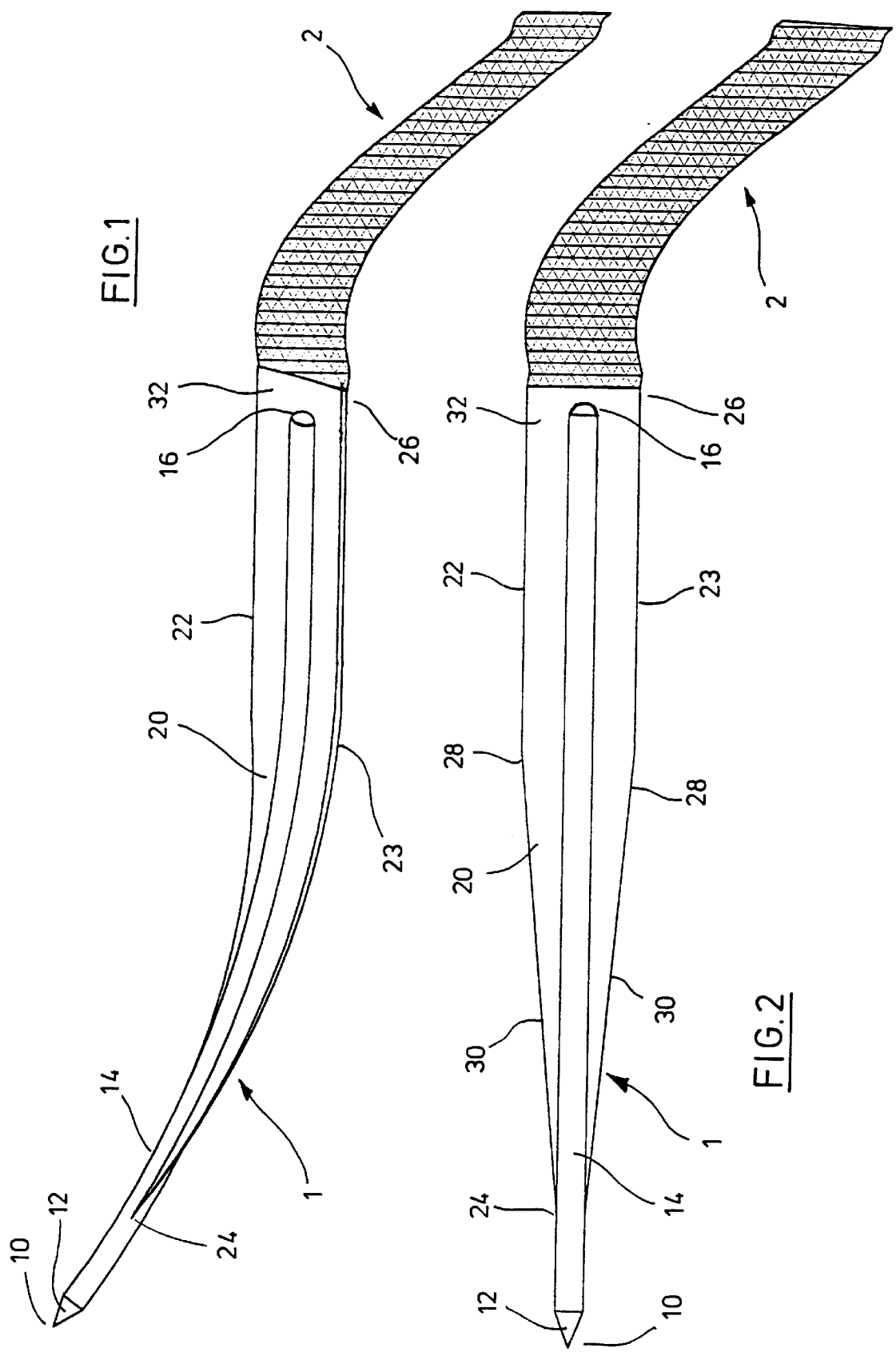

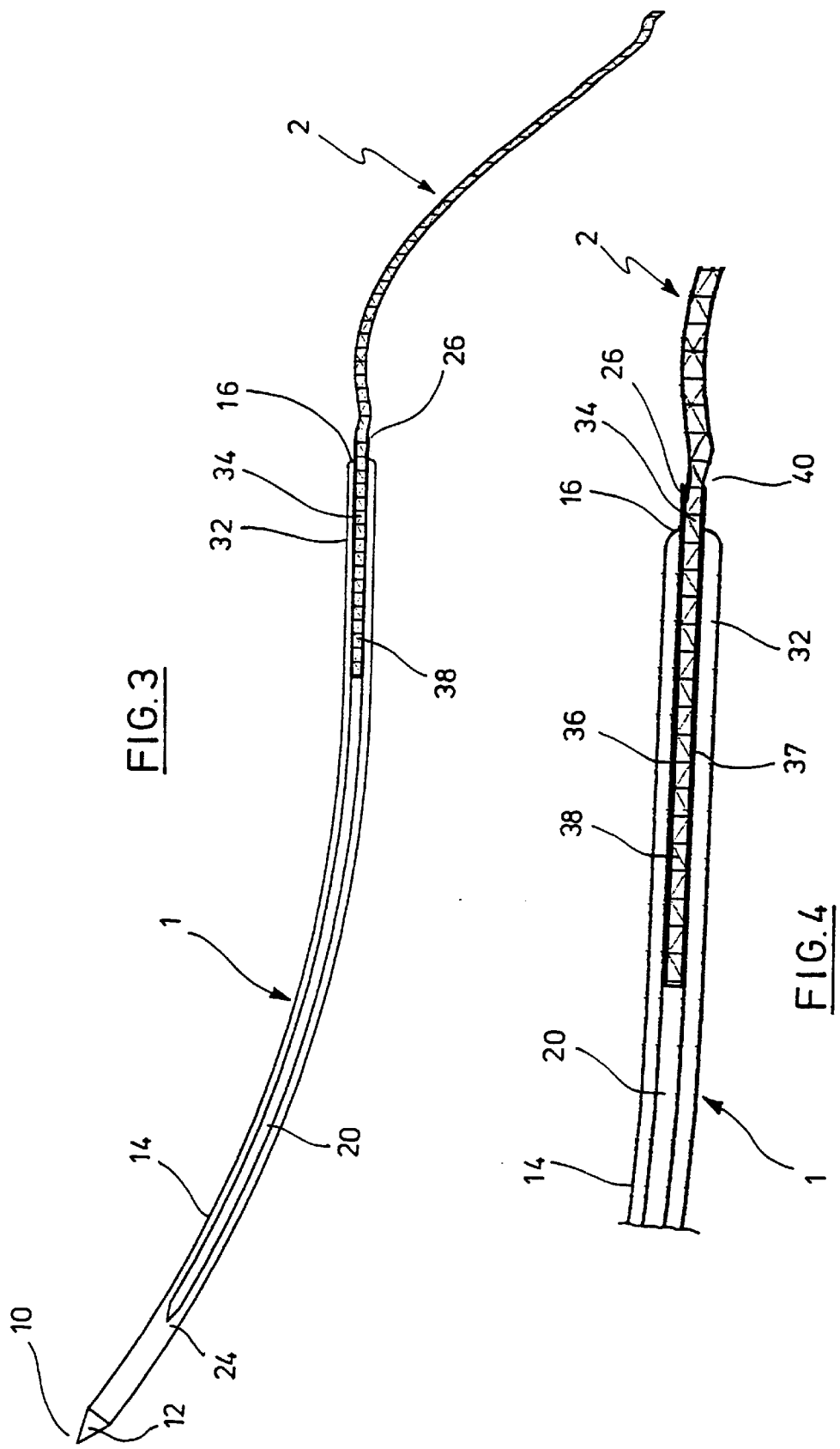

SURGICAL NEEDLE FOR IMPLANTING A TAPE

The invention relates to a surgical needle for implanting a tape.

In order to insert a surgical implant in the form of a tape (band), it is often necessary to guide the tape through tissue, e.g. near to the point where it is to be anchored to the tissue. In a conventional operating technique, a surgical needle matched to the size of the tape with a needle tip at its distal end and a shaft is used for this purpose. The tape is secured in the area of the proximal end of the shaft with the help of a shrink-on tube, the tape rolling up in its end area. When the needle is pushed through the tissue at the desired point, an essentially round puncture channel forms so that the following tape comes to lie against the tissue in its rolled-up form. This is a disadvantage as a rule, as in a flat position, the tape would be better anchored or could better fulfill a supporting function.

The object of the invention is to provide a possibility to guide the tape quickly and securely through tissue during the surgical implanting of a tape, so that it is positioned in a largely flat state.

This object is achieved by a surgical needle for implanting a tape with the features of claim 1. Advantageous versions of the invention result from the dependent claims.

The surgical needle according to the invention for implanting a tape has a needle tip, which is located at the distal end of the needle, and a shaft. An insertion wing with a distal and a proximal end extends from the shaft. The insertion wing widens from its distal end in proximal direction and, in the area of its proximal end, it has an attachment device for the tape to be implanted. Preferably the tape to be implanted is secured to the attachment device upon supply of the surgical needle.

When the surgical needle according to the invention is guided through tissue, the insertion wing widening in proximal direction gradually creates, in a tissue-friendly manner, a channel which can be largely matched to the cross-section of the tape depending on the dimensions of the insertion wing and the tape. In other words, with a flat tape the insertion wing is preferably not or not much thicker than the tape, and also the attachment device preferably has no parts significantly projecting vis-à-vis the cross-section of the tape. The surgical needle according to the invention ensures that the tape penetrates the tissue in a largely flat form and thus rolls up only slightly or not all. A largely optimal positioning of the tape is thus guaranteed. This means that the surgeon can work quickly and safely.

In a preferred version of the invention, the insertion wing is formed as a double wing with two halves, both halves preferably being arranged symmetrical to the shaft. Versions with a single insertion wing are also conceivable.

The width of the insertion wing at its distal end preferably corresponds to the width of the shaft. The width of the insertion wing in the area of its proximal end is preferably at least 70% of the width of the tape to be implanted and can be, e.g., 90% to 110% of the width of the tape to be implanted. In this version, the insertion wing starts at its distal end without abrupt transition at the shaft of the needle and increases its width in proximal direction to a size which largely corresponds to the width of the tape to be implanted. Thus, when the surgical needle is guided through tissue, the insertion wing can create the channel required for the tape in a particularly tissue-friendly manner and with a width which is sufficiently large for the tape but which does not put an unnecessary strain on the tissue.

Seen in proximal direction, the insertion wing can already reach its greatest width before reaching its proximal end. For example, its outer edge can run parallel to the shaft after reaching the greatest width. However, versions are also conceivable in which the insertion wing tapers again as it advances further in proximal direction.

In a preferred version, the distal end of the insertion wing is located in the distal third of the shaft, i.e. in the front third of the shaft adjoining the needle tip. The insertion wing can however also start further back, i.e. more towards the proximal end of the needle. This can be advantageous, e.g., if a thicker layer of tissue first needs to be completely pierced with the needle tip and the distal area of the shaft, before the insertion wing is pulled through the tissue with the help of the distal area of the needle.

The edge of the insertion wing facing the needle tip can be formed as a cutting edge. In this case, it is particularly easy to guide the surgical needle including the insertion wing through tissue.

Versions are conceivable in which the area of the proximal end of the insertion wing extends beyond the shaft. Depending on the version of the attachment device, this can have advantages, e.g. if the proximal end area of the shaft would otherwise disturb the geometry of the attachment device.

In a preferred version of the surgical needle according to the invention, the attachment device has a slit for the tape to be implanted, formed in the area of the proximal end of the insertion wing. The insertion wing is preferably designed with a double wall in the area of its proximal end, and the slit is formed between the two wall halves. In this case, the slit extends essentially parallel to the proximal area of the insertion wing and the two wall halves form a kind of plates between which the end of the tape can be secured. The tape can, e.g., be clamped, glued or sealed in the slit. Other versions of the attachment device are also conceivable; e.g. the tape can be clamped, as in a cable terminal.

There are various possibilities for connecting the insertion wing or the individual parts of the insertion wing to the shaft during the manufacture of the surgical needle. The insertion wing can, e.g., be welded to the shaft. The shaft and the insertion wing can also be formed as a unit, e.g. in one piece or so that the shaft is not an independent component with respect to the insertion wing in the area of the insertion wing.

The surgical needle can be straight or curved. If the needle is curved, then the course of the insertion wing is preferably adapted to the curvature of the shaft.

The surgical needle according to the invention can be adapted to numerous surgical possibilities through the choice of its basic shape, its dimensions and the form of the insertion wing, also in adaption to the tape to be implanted.

In the following, the invention is explained in more detail with reference to an embodiment. The diagrams show in FIG. 1 a perspective view of a surgical needle according to the invention with a tape secured to it;

FIG. 2 a top view of the surgical needle from FIG. 1,

FIG. 3 a side view of the surgical needle from FIG. 1, and

FIG. 4 an enlarged section from FIG. 3.

A version of a surgical needle 1 for implanting a tape 2 is shown in FIGS. 1 to 4. The tape 2 is secured to the surgical needle 1.

The surgical needle 1 has a distal end 10, where the needle tip 12 is located, and a shaft 14, whose proximal end is numbered 16.

An insertion wing 20, which is formed as a double wing with two halves 22 and 23, extends from the shaft 14. The insertion wing 20 extends from a distal end 24, which is located not far from the needle tip 12 in the embodiment, to a proximal end 26, which is located beyond the proximal end 16 of the shaft 14. The two halves 22, 23 of the insertion wing 20 gradually widen in the zone between the distal end 24 of the insertion wing 20 and a position 28 from the width of the shaft 14 (which has a circular cross-section in the embodiment) up to the width of the tape 2. In this zone the edges 30 of the halves 22, 23 of the insertion wing 20 facing the needle tip 12 can be designed as a cutting edge. The insertion wing 20 maintains its width between the points 28 and the proximal end 26. The insertion wing 20 is designed flat, i.e. it is not significantly thicker than the tape 2 in the embodiment. The course of the insertion wing 20 is adapted to the curvature of the shaft 14 of the surgical needle 1 which is curved in the embodiment.

In the area of its proximal end 26, the insertion wing 20 has an attachment device 32, as can best be seen in the side view according to FIG. 3 and the enlarged section in FIG. 4. In the embodiment, the attachment device 32 has a slit 34 which is formed in the proximal area of the two halves 22, 23 of the insertion wing 20. In other words, in this area the insertion wing 20 is designed with a double wall with two wall halves 36 and 37 which are drawn in bold lines in FIG. 4, and the slit 34 is located between these wall halves 36 and 37.

The end zone 38 of the tape 2 is inserted into the slit 34. As, in the embodiment, the thickness of the insertion wing 20 and thus the distance between the outsides of the two wall halves 36 and 37 is only slightly greater than the thickness of the tape 2, the tape 2 is compressed in its end zone 38 inside the slit 34 and, in a transition area 40 outside the slit 34, assumes its thickness when in a free state, see FIG. 4.

In the embodiment, the tape 2 is secured to the surgical needle 1, the procedure being that the slit 34, which extends over the entire width of the insertion wing 20, is bent open somewhat, then the end zone 38 of the tape 2 is inserted together with adhesive and finally the slit 34, i.e. the proximal area of the insertion wing 20 and of the shaft 14, is compressed. The tape 2 is then securely connected to the surgical needle 1.

What is claimed is:

1. A surgical needle device, comprising:
   a substantially round shaft;
   a needle tip extending from a distal end of the shaft;
   an attachment device extending from a proximal end of the shaft;
   an insertion wing extending outwardly from the shaft and having a distal end and a proximal end and widening in the proximal direction; and
   a substantially flat tape to be implanted coupled to the attachment device, the tape having a width greater than a diameter of the shaft,
   wherein a width of the proximal end of the insertion wing is at least 70% of the width of the tape.

2. The surgical needle device according to claim 1, wherein the distal end of the insertion wing has a width substantially equal to the diameter of the shaft.

3. The surgical needle device according to claim 1, wherein a cross-section of the insertion wing at its proximal end is at least substantially equal to a cross-section of the tape.

4. The surgical needle device according to claim 1, wherein the width of the insertion wing at the proximal end is 90 percent to 110 percent of the width of the tape to be implanted.

5. The surgical needle device according to claim 1, wherein a thickness of the insertion wing is less than the diameter of the shaft.

6. The surgical needle device according to claim 1, wherein the insertion wing is formed as a double wing with first and second halves, the first and second halves being arranged symmetrical to the shaft.

7. The surgical needle device according to claim 1, wherein the insertion wing and shaft are formed as an integral unit.

8. The surgical needle device according to claim 1, wherein the needle is curved, and the insertion wing is adapted to the curvature of the shaft.

9. A surgical needle assembly comprising:
   a needle having a proximal end, a needle tip at a distal end, and a substantially round shaft from which an insertion wing with a distal end and a proximal end extends, the insertion wing widening in the proximal direction and having a width at its distal end substantially equal to a diameter of the shaft; and
   a substantially flat tape to be implanted having a width greater than the diameter of the shaft; and
   wherein, in the area of its proximal end, the width of the insertion wing is at least 70% of the width of the tape, and wherein the needle further comprises an attachment device in the area of its proximal end capable of receiving the tape to couple the tape thereto.

10. Surgical needle according to claim 9, wherein in the area of its proximal end, the width of the insertion wing is 90% to 110% of the width of said tape.

11. Surgical needle according to claim 9, wherein, seen in its proximal direction, the insertion wing reaches its greatest width before it reaches its proximal end.

12. Surgical needle according to claim 9, wherein the distal end of the insertion wing is located in the distal third of the shaft.

13. Surgical needle according to claim 9, wherein the proximal end of the insertion wing extends beyond the shaft.

14. Surgical needle according to claim 9, wherein an edge of the insertion wing facing the needle tip is formed as a cutting edge.

15. Surgical needle according to claim 9, wherein the attachment device for the tape to be implanted has a slit, which is formed in the area of the proximal end of the insertion wing.

16. Surgical needle according to claim 15, wherein the insertion wing further comprises a double wall having first and second wall halves in the area of its proximal end and the slit is formed between the first and second wall halves.

17. Surgical needle according to claim 9, wherein the shaft and the insertion wing are formed as an integral unit.

18. Surgical needle according to claim 9, wherein the needle is curved, and the course of the insertion wing is adapted to the curvature of the shaft.

* * * * *